United States Patent [19]

Olson et al.

[11] 4,022,807

[45] May 10, 1977

[54] VITAMIN A ESTERS

[75] Inventors: Gary Lee Olson, Westfield; Gabriel Saucy, Essex Fells, both of N.J.

[73] Assignee: Hoffmann-La Roche Inc., Nutley, N.J.

[22] Filed: Aug. 11, 1975

[21] Appl. No.: 603,480

Related U.S. Application Data

[60] Division of Ser. No. 464,398, April 26, 1974, Pat. No. 3,928,400, and a continuation-in-part of Ser. No. 303,162, Nov. 2, 1972, abandoned.

[52] U.S. Cl. .......................... 260/410; 260/617 A; 260/488 A; 260/476 R
[51] Int. Cl.² ...................... C09F 5/08; C09F 7/10
[58] Field of Search ....... 260/410, 410.9 V, 617 A, 260/488 A, 476 R, 475 N

[56] References Cited

UNITED STATES PATENTS

| | | | |
|---|---|---|---|
| 2,705,728 | 4/1955 | Inhoffen | 260/617 A |
| 2,712,515 | 7/1955 | Beutel | 260/617 A |

FOREIGN PATENTS OR APPLICATIONS

| | | | |
|---|---|---|---|
| 696,235 | 8/1953 | United Kingdom | 260/617 A |
| 692,162 | 5/1953 | United Kingdom | 260/617 A |
| 665,147 | 1/1952 | United Kingdom | 260/617 A |

*Primary Examiner*—Winston A. Douglas
*Assistant Examiner*—John F. Niebling
*Attorney, Agent, or Firm*—Samuel L. Welt; Bernard S. Leon; William H. Epstein

[57] ABSTRACT

A process for producing vitamin A esters, vitamin A aldehyde and vitamin A acid esters from esters of 3,7-dimethyl-9-(1-hydroxy-2,2,6-trimethylcyclohexyl)-nona-2,4,6-trien-8-yn-1-ol and 3,7-dimethyl-9-(1-hydroxy-2,2,6-trimethylcyclohexyl)-nona-2,4,6-trien-8-ynoic acid including intermediates in this process.

9 Claims, No Drawings

VITAMIN A ESTERS

CROSS REFERENCE TO RELATED APPLICATIONS.

This is a division, of application Ser. no. 464,398 filed Apr. 26, 1974 now U.S. Pat. No. 3,928,400.

This application is a continuation-in-part application of U.S. Patent Application Ser. No. 303,162, filed Nov. 2, 1972, Olson and Saucy now abandoned.

SUMMARY OF THE INVENTION

In accordance with this invention, vitamin A esters and vitamin A acid ester type compounds which have the formula:

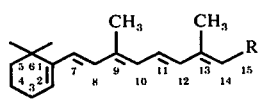   I wherein
R is —CH$_2$OH, —CHO, —CH$_2$OR$_1$ or

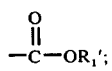

R$_1$ is alkanoyl or aroyl; and R$_1$' is alkyl, aryl or aralkyl;
can be prepared from compounds of the formula:

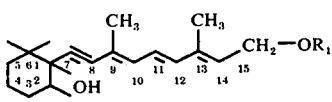   II wherein
R$_1$ is as above;
and compounds of the formula:

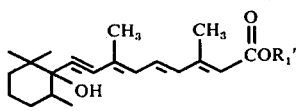   III wherein
R$_1$' is as above.

This process provides a method for synthetically producing all trans vitamin A compounds of the formula I from the compounds of formulae II or III irrespective of the cis/trans configuration about the double bonds in the compounds of formulae II and III.

DETAILED DESCRIPTION OF THE INVENTION

The numbering of the carbon atoms in the various formulae set forth throughout this application is given for the purpose of convenience only.

The term "halogen" includes all four halogens, i.e., iodine, bromine, chlorine and fluorine, with bromine and chlorine being preferred. The term "lower alkyl" as used throughout this application comprehends both straight and branched chain hydrocarbon groups containing from 1 to 6 carbon atoms such as methyl, ethyl, propyl and isopropyl. The term "alkyl" includes lower alkyl containing from 1 to 8 carbon atoms as well as higher alkyl groups which contain from 7 to 18 carbon atoms such as decyl, hexadecyl, octadecyl, octyl, nonyl, dodecyl, etc. The term "lower alkoxy" as used throughout this application comprehends lower alkoxy groups containing from 1 to 6 carbon atoms such as methoxy, propoxy, ethoxy, etc., preferably methoxy or ethoxy. The term "cycloalkyl" comprehends cycloaliphatic groups having a ring of from 3 to 7 carbon atoms such as cyclopropyl, cyclopentyl and cyclohexyl, which can be unsubstituted or substituted in one or more positions with a lower alkyl group. The "cyclo alkyl groups" can contain from 3 to 15 carbon atoms.

The term "aryl" as used throughout this application includes mono-nuclear aryl groups such as phenyl which can be substituted or unsubstituted in one or more positions with lower alkyl, or an electron withdrawing group such as carboxy, formyl, trifluoromethyl, alkanoyl, phenyl, alkoxycarbonyl, halogen, nitro, or polynuclear aryl groups such as naphthyl, anthryl, phenanthryl, azulyl, etc., which may be substituted with one or more of the aforementioned groups. The preferred aryl radical is phneyl, or phenyl substituted with lower alkyl, nitro, cyano, trifluoromethyl, or halogen.

The term "aralkyl" denotes aryl lower alkyl groups wherein aryl and lower alkyl are defined as above. The preferred aralkyl group is benzyl. The term "aroyl" denotes the group $$\text{"aryl}-\underset{\underset{O}{\|}}{C}-\text{"}$$

wherein aryl is defined as above. The preferred aroyl group is benzoyl.

The term "alkanoyl" includes lower alkanoyl groups containing from 2 to 6 carbon atoms such as acetyl, propionyl, butyryl, etc., as well as higher alkanoyl groups containing from 7 to 18 carbon atoms such as palmitoyl, pentadecanoyl, octadecanoyl, octanoyl, decanoyl, etc.

In accordance with this invention, the compound of formula II can be converted to a vitamin A compound of the formula:

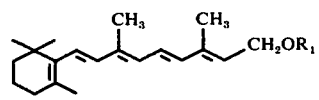   I-A wherein
R$_1$ is as above;
by the following reaction scheme:

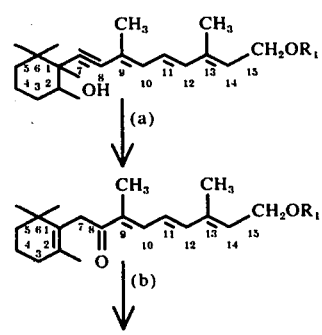

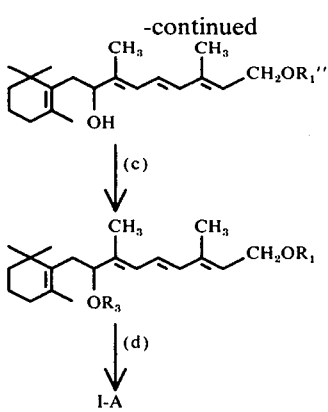

wherein —OR$_3$ is —OH or a leaving group or aroyl; and R$_1$ is as above; and R$_1''$ is hydrogen, alkanoyl or aroyl.

The compound of formula II is converted to the compound of formula IV, via step (a), by heating the compound of formula II in an inert organic solvent in the presence of an organo-silicon vanadate of the formula:

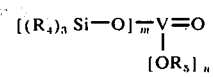

wherein R$_4$ is alkyl, cycloalkyl, aryl, aryl lower alkyl, or cycloalkyl substituted lower alkyl; R$_5$ is R$_4$ or:

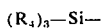

$m$ is an integer from 1 to 3; and $n$ is an interger of from 0 to 2; with the proviso that the sum of $m$ and $n$ is 3.

Among the preferred organo silicon vanadate catalysts of this invention are catalysts of the formula:

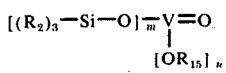

wherein
R$_2$ is phenyl or phenyl substituted in one or more positions with an electron withdrawing group;
R$_{15}$ is lower alkyl, cycloalkyl, phenyl, or phenyl lower alkyl;

—Si (R′$_2$)$_3$ or —Si (R′$_4$)$_3$;

wherein R′$_2$ is phenyl substituted in one or more positions with an electron withdrawing group; R′$_4$ is lower alkyl, cycloalkyl, phenyl or phenyl lower alkyl; and $m$ and $n$ are as above.

Where R$_2$ or R$_{15}$ is phenyl substituted in one or more positions with an electron withdrawing group, any conventional electron withdrawing group can be utilized. Among the preferred electron withdrawing groups are those disclosed on page 651 of Fieser and Fieser, *Textbook of Organic Chemistry,* 1954 Edition. These groups are:
—NO$_2$;
—CN;
—COCH$_3$;
—CHO;
—COOC$_2$H$_5$;
—Cl;
—Br;
—I; and
—COOH Also included among the preferred electron withdrawing groups are —F, —CF$_3$, and —C$_6$H$_5$.

Among the organo silicon vanadate catalysts which are preferred are the compounds where R$_4$ is lower alkyl (particularly methyl, ethyl, isopropyl or n-butyl), naphthyl, phenyl (particularly phenyl), lower alkyl substituted phenyl (particularly tolyl or xylyl), nitro substituted phenyl (particularly m-nitrophenyl or 3,5-dinitrophenyl); halogen substituted phenyl (particularly perfluorophenyl), and trifluoromethyl substituted phenyl (particularly m-trifluoromethylphenyl), or unsubstituted phenyl lower alkyl (particularly benzyl or phenethyl). Among the preferred organo silicon vanadata catalysts, particularly preferred are the compounds wherein $m$ is 3 and $n$ is 0, quite particularly tris-(trimethyl-siloxy)-vanadium oxide, tris-(triphenyl-siloxy)-vanadium oxide, and tris-(3-nitrophenyl-siloxy) vanadium oxide.

The organo silicon vanadate catalyst can be prepared according to known methods. The catalysts can be prepared, for example, according to one of the following procedures:

i. the reaction of, for example, vanadium pentoxide with for example, a trialkyl silanol of the formula [alkyl]$_3$—SiOH or a triaryl silanol of the formula [aryl[-$_3$SiOH with azeotropic removal of the water formed in the reaction with the aid of an entraining agent such as, for example, benzene;

ii. the reaction of, for example, vanadium oxytrichloride with, for example, a trialkyl silanol or triaryl silanol in the presence of a base such as pyridine or ammonia;

iii. the reaction of, for example, vanadium oxytrichloride with, for example, a trialkyl alkali silanolate of the formula [alkyl]$_3$SiOMe(I) or a triaryl alkali silanolate of the formula [aryl]$_3$SiOMe(I); where Me is an alkali meal;

iv. the reaction of, for example, a vanadium acid ester of the formula [alkoxy]$_3$—V=O with, for example, a trialkyl silanol or triaryl silanol, if desired in the presence of catalytic amounts of an alkyl- or aryl alkali silanolate (e.g., a trialkyl alkali silanolate);

v. the reaction of, for example, silver orthovanadate of the formula Ag$_3$VO$_4$, with for example, a trialkyl silyl halide fo the formula [alkyl]$_3$SiCl or a triaryl silyl halide of the formula [aryl]$_3$SiCl in a solvent such as for example, benzene or methylene chloride;

vi. the reaction of, for example, vanadium pentoxide with, for example, a hexaalkyl disiloxane of the formula [alkyl]$_3$SiOSi[alkyl]$_3$ at an elevated temperature, for example, at about 100° C.; and vii. the double reaction of a vanadium acid ester of the formula [alkoxy]$_3$—V=O with a silyl ester of the formula (R$_4$)$_3$ Si—O—CO R'' where R is lower alkyl, where R$_4$ is as above, for example, with tripropyl orthovanadate with the expulsion of propyl acetate preferably in a solvent, such as n-heptane, with which the ester provided in the reaction forms an azeotrope that can be separated from the reaction medium.

The reaction step of (a) is carried out in an inert organic solvent. In carrying out this reaction, any conventional inert organic high-boiling solvents can be utilized, i.e., solvents boiling above 35° C. Among the preferred solvents are included aliphatic hydrocarbons, particularly cyclododecane, decalin, paraffin and paraffin oil; aromatic hydrocarbons, particularly toluene and xylene; ethers, particularly anisole and dioxane.

In carrying out the reaction of step (a) temperatures of 35° C. or above are utilized. The reaction is expeditiously carried out at a temperature of from 60° to 200° C., with a temperature of about 80° to 170° C. being generally utilized. Generally, it is preferred to carry out this reaction at the reflux temperature. If desired, the reaction can also be carried out under pressure, in which case pressures up to about 50 atmospheres can be used. In the case where pressure is utilized, low boiling solvents which include lower aliphatic and aromatic hydrocarbons such as benzene, heptane and cyclohexane can be used.

In some cases in the reaction of step (a), a compound of the formula:

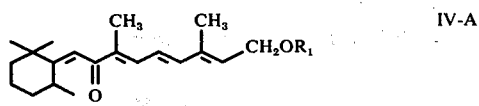

wherein $R_1$ is as above;
is formed in admixture with the compound of formula IV. The yield of the compound of formula IV in this mixture can be increased by heating the compound of formula IV-A to the reflux temperature of the reaction medium for a period of at least 30 minutes to convert the compound of formula IV-A to the compound of formula IV. If desired, heating times of 20 hours or longer can be utilized. However, since such long heating times do not increase the yields of the compound of formula IV, the use of long heating times is not economic.

On the other hand, the mixture containing the compound of formula IV and formula IV-A can be converted via steps (b), (c) and (d) to the compound of formula I-A with the compound of formula IV-A being transformed into the following intermediates:

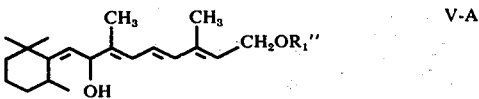

wherein $R_1''$ is as above;
and

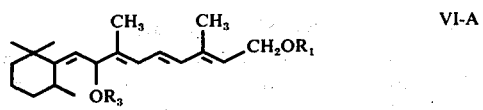

wherein $R_3$ is as above.

In accordance with another preferred embodiment of this invention, the reaction of step (a) is carried out utilizing an organo silicon vanadate catalyst described hereinbefore and in the presence of a silanol of the formula:

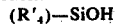

wherein $R'_4$ is alkyl, aryl, cycloalkyl, aryl lower alkyl, cycloalkyl-substituted lower alkyl.

The silanol can be present in the reaction medium in an amount of at least 0.01 mole % of the compound of formula II above. On the other hand, the silanol can be utilized as the solvent medium. Generally, it is preferred to utilize the silanol in an amount of from 5 to 65 mole % based upon the moles of the compound of formula II above.

The compound of formula II can exist in various isomeric forms due to the double bond at the 9–10, 11–12 and 13–14 positions. Therefore, the compound of formula II can exist in the following stereoisomeric forms:

9-trans,11-trans,13-trans;
9-cis,11-trans,13-trans;
9-trans,11-trans,13-cis;
9-trans,11-cis,13-cis;
9-cis,11-cis,13-trans;
9-cis,11-cis,13-cis;
9-trans,11-cis,13-trans; and
9-cis,11-trans,13-cis;

or as mixtures of the above isomers.

The reaction of step (a) does not substantially change the geometrical configuration of the double bonds in the compound of formula II. Therefore, the compound of formula IV has substantially the same geometrical configuration as the compound of formula II. If the compound of the formula II is a mixture of geometric isomers or is other than the 9-trans,11-trans,13-trans isomer, the compound of formula IV can be isomerized to produce the all trans isomeric form of the compound of the formula IV. This reaction can be carried out by treating the compound of formula IV with an organic acid or an organic amine base at temperatures of from 20° to 160° C. In carrying out this isomerization reaction, any organic acids which include aroic acids such as benzoic acid or lower alkanoic acids, such as acetic acid can be utilized. Among the preferred lower alkanoic acids for use in isomerizing the compound of formula IV are included acetic acid, propionic acid, etc. On the other hand, this reaction can be carried out by utilizing an organic base such as a tertiary organic amine base or a quaternary amine base. Among the preferred organic amine bases are included pyridine, piperidine acetate, triethylamine, trimethylamine, diazabicycli-[2,2,2]-octane, tetramethylammonium acetate, etc. In carrying out this reaction, no solvents need be present since the organic acid or the organic amine bases can be utilized as the solvent medium. On the other hand, any conventional inert organic solvent can be added to the reaction mixture, if desired. Among the solvents which may, if desired, be added to the reaction mixtures are included the aromatic solvents such as benzene, toluene, etc., or the solvents hereinbefore mentioned. Among the preferred solvents for use in this reaction are the aromatic solvents such as benzene as well as the other solvents mentioned hereinbefore.

A compound of the formula IV is converted to the compound of formula V by reducing the compound of formula IV. Any conventional method for reducing ketones to alcohols can be used to carry out this method. A method of carrying out the reaction of step (b) is by the use of reducing agents. Any reducing agent conventionally utilized for converting ketones to alcohols can be used to carry out the reaction of step (b). Among the preferred reducing agents are the complex metal hydrides. Any conventional complex metal hydride reducing agent could be utilized in carrying out this reaction. Among the complex metal hydrides there can be used, for example, an alkali metal borohydride such as sodium borohydride or lithium borohydride, alkaline earth metal borohydrides such as calcium borohydride and alkali metal aluminum hydrides such as lithium aluminum hydride or diisobutyl aluminum hydride, preferably sodium dihydro-bis(2-methoxyethoxy) aluminum. This reduction is carried out in an inert organic solvent medium. Any conventional inert organic solvent can be utilized in carrying out this reaction. Among the preferred inert organic solvents are included, tetrahydrofuran, dioxane, diethyl ether, hexane, toluene, benzene or xylene. In carrying out this reduction reaction, temperature and pressure are not critical and this reaction can be carried out at room temperature and atmospheric pressure. On the other hand, elevated or reduced temperatures can be utilized. Generally, this reaction is carried out at a temperature of from −70° C. to about 80° C. By utilizing a complex metal hydride, the compound of formula IV is generally converted to a compound of formula V where $R_1''$ is hydrogen. Another method of carrying out this procedure is by catalytic hydrogenation, i.e., hydrogen gas in the presence of a noble metal catalyst. By utilizing catalytic hydrogenation, the compound of formula IV is converted to the compound of formula V where $R_1''$ is alkanoyl or aroyl.

The compound of formula V can, in accordance with one embodiment of the invention, be converted to the compound of formula VI by converting the hydroxy group on position 8 of the compound of formula V to a leaving group. This can be accomplished where $R_1''$ in the compound of formula V is alkanoyl or aroyl. Any conventional leaving group can be utilized in this procedure. Among the preferred leaving groups formed by $-OR_3$ are alkylsulfonyloxy such as methyleulfonyloxy, arylsulfonyloxy such as p-toluenesulfonyloxy, alkanoyloxy or aroyloxy such as benzyloxy. Any conventional method of converting a hydroxy group to a leaving group can be utilized in the formation of the compound of formula VI.

Where $R_1''$ in the compound of formula V is hydrogen, the compound of formula V maybe treated with an acylating agent such as a lower alkanoylating or aroylating agent. In general, this reaction is carried out by treating the compound of formula V with an organic acid anhydride or a functional derivative of an organic acid. The preferred organic acids are lower alkanoic acids, particularly acetic acid and benzoic acid. Any of the conditions conventional in esterifying hydroxy groups can be utilized in converting the compound of formula V where $R_1''$ is hydrogen to the compound of formula VI. If one mole of the acylating agens is utilized per mole of the commpound of formula V where $R_1''$ is hydrogen, the hydroxy group at the 15-position is esterified. On the other hand, if two or more moles of the acylating agent are utilized per mole of the compound of formula V, both the hydroxy groups at the 8 and 15 positions can be esterified.

The compound of formula VI is converted to the compound of formula I-A by treating the compound of formula VI with a dehydrating agent. In carrying out this reaction, any conventional dehydrating agent cant be utilized. Among the preferred dehydrating agents are included thionyl chloride, phosphorous oxy-chlorie; inorganic acids such as sulfuric acid, hdyrogen bromide, hydrogen chloride, etc; strong organic acids such as p-toluene sulfonic acid; alkyl sulfonic acids such as methane sulfonic acid. Generally, this reaction is carried out in an inert organic solvent. Any conventional inert organic solvent can be utilized in carrying out this reaction. Among the preferred inert organic solvents when thionyl chloride and phosphorous oxychloride are utilized, is pyridine. On the other hand, when hydrogen bromide is utilized, methylene chloride or chloroform are the preferred solvents. The dehydration produces a trans configuration about the 7–8 double bond in the compound of formula I-A.

If desired, the vitamin A ester of formula I-A can be converted to the corresponding alcohol by conventional hydrolysis or reduction procedures well known in the art.

The compound of formula III can be converted to a vitamin A acid ester of the formula:

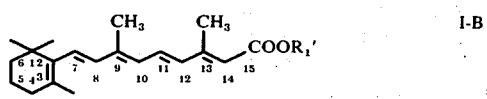

wherein $R_1''$ is as above;
by the following reaction scheme:

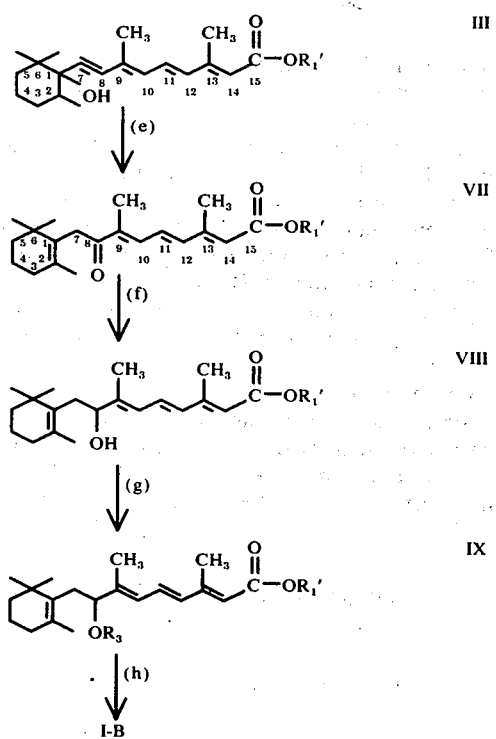

wherein $R_1''$ and $-OR_3$ are as above.

The compound of formula III is converted to the compound of formula VII, via reaction step (c), by heating the compound of formula III in the presence of an organo-silicon vanadate catalyst described in connection with step (a). The reaction step (c) is carried out utilizing the same reaction conditions described in connection with the reaction step (a). The preferred method for carrying out this reaction step is to utilize the aforementioned organo-silicon vanadate catalyst in the presence of a silanol such as described in reaction step (a). In the reaction step (e), a compound of the formula:

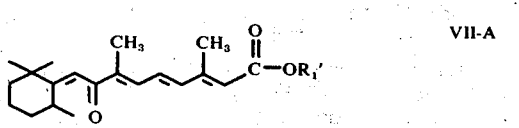

wherein $R_1'$ is as above;

can be formed in admixture with the compound of formula VII. The yield of the compound of formula VII in this mixture can be increased in the same manner as described in connection with reaction step (a). On the other hand, a mixture containing the copound of formulae VII and VII-A can be converted via reaction steps (f), (g) and (h) to the compound of formula I-B with the compound of formula VII-A being converted to the following intermediates:

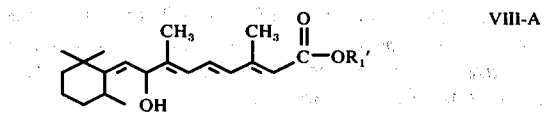

wherein $R_1'$ is as above; and

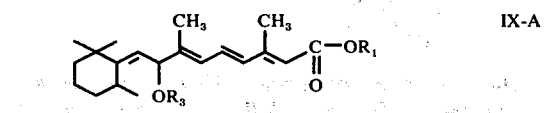

wherein $R_3$ and $R_1'$ are as above.

The compound of formula III can exist in all of its possible geometric isomeric forms as well as mixtures thereof.

Where the compound of formula VII exists as an isomeric mixture or where it is in an isomeric form other than the 9, 11 and 13-transform, the compound of formula VII may be isomerized to its all trans form by treatment with an organo acid or an organic amine base in the same manner described in connection with the isomerization of the compound of the formula IV. This isomerization is carried out in the same manner described in connection with the isomerization of the compound of the formula IV. The compound of the formula VII can be converted to a compound of the formula VIII by reducing the compound of the formula VII, as in step (b), by catalytic hydrogenation or preferably with sodium borohydride. Reduction with sodium borohydride is carried out in the same manner as described in connection with step (b). When sodium borohydride is utilized, only the keto group at the 8 position of the compound of formula VII is reduced. The ester linkage

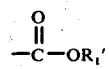

is not effected by this reduction. The compound of the formula VIII may be converted, if desired, to the compound of the formula IX via reaction step (g) by converting the free hydroxy group to a leaving group. The same techniques, leaving groups and conditions described in connection with reaction step (c) can be utilized in carrying out this conversion. The compound of formula IX, either containing a free hydroxy group or with a leaving group substituted thereon, is converted to the compound of formula I-B by treating the compound of formula IX with a dehydrating agent in the same manner described in connection with reaction step (d). This reaction produces a trans configuration across the double bond at the 7-8 positions on the compound of the formula I-B.

The compound of formula II can exist in an isomeric form where there is a cis configuration across the 9-10 double bond and a trans configuration across the 11-12 double bond. This compound can be prepared via the following reaction scheme:

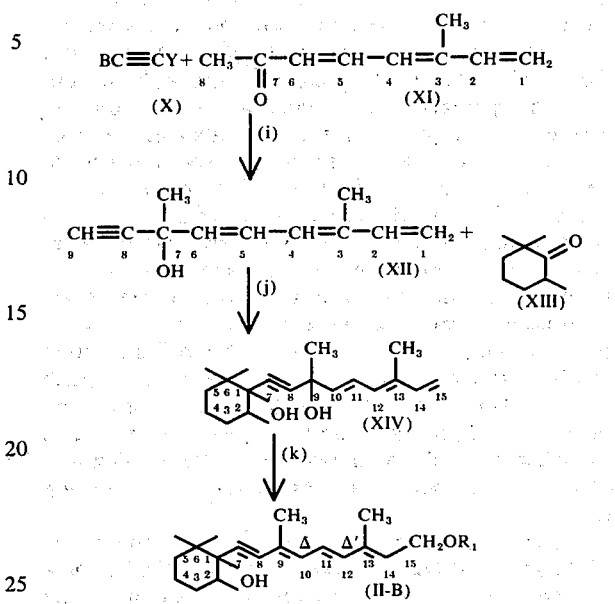

wherein $R_1$ is as above; Y is lithium, sodium or MgX; and X is chlorino, bromine or iodine; $\Delta$ represents a cis configuration; and $\Delta'$ represents a trans configuration.

The compound of formula X is reacted with the compound of formula XI via a Grignard reaction to produce the compound of formula XII. In carrying out this reaction, any of the conditions which are conventional for carrying out Grignard reactions can be utilized. Generally, this reaction is carried out in an inert organic solvent medium. Among the preferred solvents are diethyl ether and tetrahydrofuran. In carrying out this reaction, temperature and pressure are not critical and this reaction can be carried out at room temperature and atmospheric pressure. On the other hand, elevated temperatures and pressures can be utilized. Generally, it is preferred to carry out this reaction at a temperature range of from 20° to 40° C. Conveniently, moisture is excluded and the reaction is carried out in an atmosphere of a protecting gas, preferably nitrogen.

In carrying out the reaction of step (j), the compound of formula XII is converted to its salt form, i.e., a compound of the formula:

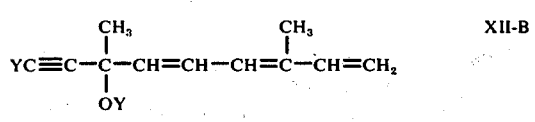

wherein Y is as above.

The compound of formula XII-B is reacted with a compound of formula XIII under conditions conventional for Grignard reactions to form a compound of the formula XIV. This reaction is carried out in the same manner as described in connection with step (i) with a mixture of diethyl ether and benzene being the preferred solvent.

The compound of formula XIV is converted to the compound of formula II-B via step (k), by treating the compound of formula XIV with an alkanoic acid or an aroic acid. Any conventional alkanoic acid containing from 2–18 carbon atoms can be utilized to carry out this reaction. Among the preferred alkanoic aids which can be utilized to carry out this reaction are included acetic acid, propionic acid, palmitic acid, pentadecanoic acid, octadecanoic acid, decanoic acid, etc. Any conventional aroic acid can be utilized to carry out this reaction. Among the preferred aroic acids are benzoic acid, phthalic acid, p-phenylazobenzoic acid. In carrying out this reaction, the lower alkanoic or aroic acid can act as the solvent medium. On the other hand, this reaction, can, if desired, by carried out in an inert organic solvent medium. Any conventional inert organic solvent can be utilized as the reaction medium. Among the preferred solvents which can be utilized are included benzene, toluene, as well as the solvents hereinbefore mentioned. In carrying out this reaction, temperature and pressure are not critical and this reaction can be carried out at room temperature and atmosperic pressure. On the otherhand, if desired, elevated temperatures and pressures can be utilized. Temperatures as high as the reflux temperatures of the reaction medium can be utilized in carrying out the reaction of step (k).

The stereoconfiguration of the double bond at the 11–12 and 13–14 positions in the compound of formula II-B does not depend upon the configuration of the double bend at the 3–4 position in the compound of formula XI. The configuration of the double bond at the 3–4 position in the compound of formula XI is unchanged by the reaction of step (i) such that the compound of formula XII has the same configuration about the 3–4 double bend as in the compound of formula XI. The same is true for the reaction of step (j), the configuration of the double bond in the 3–4 position of the compound of formula XII is the same as the configuration of the 12–13 double bond in the compound of formula XIV.

The reaction of step (k) produces the compound of formula II-B having exclusively the 9-cis, 11-trans configuration about the double bonds, regardless of whether the 12–13 double bond in the compound of formula XIV (or the 3–4 double bond in the compounds of formulae XII and XI) are cis, trans, or a mixture of cis and trans.

The compound of formula II can also be prepared from a compound of the formula:

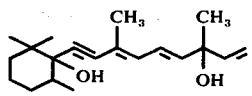

XV

This reaction is carried out by treating the compound of formula XV with an alkanoic or aroic acid in the same manner as described in connection with reaction step (k). This reaction does not effect the stereochemistry across the double bonds in the compound of formula XV.

The compound of formula XV is prepared from a compound of formula:

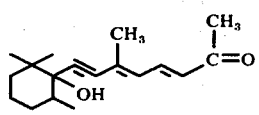

XVI

In preparing a compound of formula XV, the compound of formula XVI is reacted via a Grignard reaction with

$CH_2=CHY'$ wherein Y' is MgX or lithium; and X is as above.

Depending upon the geometrical configuration of the starting material of the formula XVI, a compound of formula II having various geometrical configurations about the double bonds can be produced. This reaction is carried out in the same manner as described in connection with reaction step (h). The preferred solvent in this reaction is a mixture of benzene and diethyl ether.

Where the compound of formula II is in any isomeric form, or is a mixture of isomers, this compound can be prepared from the compound of formula III via an intermediate of the formula:

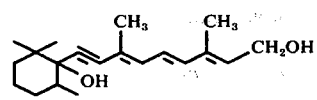

XVII

The compound of formula III is converted to the compound of formula XVII by reduction with lithiumaluminum hydride, lithium borohydride, diisobutylaluminum hydride and sodium dihydro-bis(2-methoxyethoxy)aluminum in the same manner as described in reaction step (b). The compound of formula XVII is converted to the formula II by conventional esterification procedures utilizing an alkanoylating or aroylating agent such as described in connection with the conversion of compounds of the formula V to compounds of the formula VI via reaction step (c). However, reactive derivatives of alkanoic acids containing from 2 to 18 carbon atoms can be utilized as the alkanoylating agent.

The compound of the formula III can be prepared in its various isomeric forms or as a mixture of isomers by the following reaction scheme:

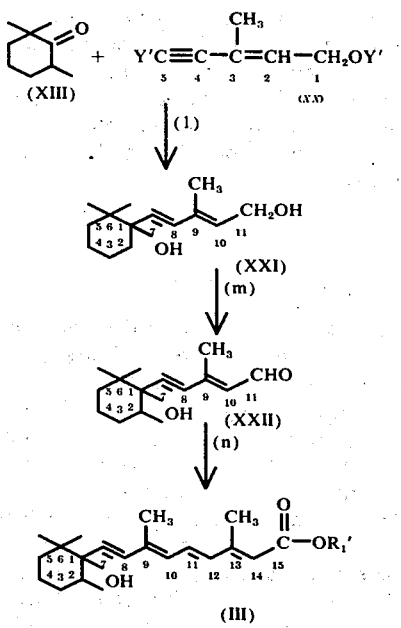

wherein $R_1'$ and Y' are as above.

The compound of formula XI is reacted with the compound of formula XX to produce a compound of formula XXI via reaction step (1). This reaction is carried out via a Grignard reaction utilizing the same conditions described in connection with reaction step (i). The preferred solvent in this reaction is a mixture of dichloromethane and diethyl ether.

The compound of formula XXI is converted to a compound of formula XXII by treating the compound of formula XXI with an oxidizing agent. Any conventional oxidizing agent capable of oxidizing an allylic alcohol to an aldehyde can be utilized in this reaction. The preferred oxidizing agents are silver salts such as silver carbonate, manganese dioxide, Jones Reagent, etc. Any of the conditions conventinally utilized with these reducing agents can be utilized in connection with the reaction of step (m).

The compound of formula III can be obtained by treating the compound of formula XXII with either a phosphorane of the formula:

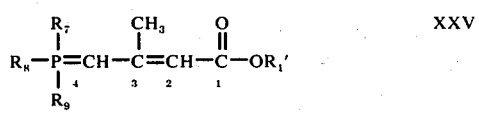

wherein $R_7$, $R_8$ and $R_9$ are aryl; and $R_1'$ is as above; or a phosphate of the formula:

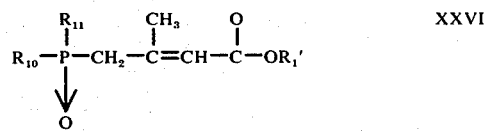

wherein $R_{10}$, and $R_{11}$ are aryloxy or lower alkoxy and $R_1'$ is as above.

The reaction of a phosphorane of formula XXV with the compound of formula XXII, can, if desired, be carried, be carried out in the presence of an organic solvent. In carrying out this reaction, any conventional organic solvent can be utilized. Among the conventional organic solvents which can be utilized in accordance with this invention are included benzene, toluene, ethylalcohol, N,N-dimethylformamide, 1,2-dimethoxyethane and dioxane. In carrying out this reaction, temperature and pressure are not critical, and this reaction can be carried out at from about 0° to about 50° C. and at atmospheric pressure.

The phosphoranes of formula XXV above can be prepared by known procedures from the corresponding phosphonium salts. In accordance with the invention, $R_7$, $R_8$ and $R_9$ can be an aryl group. The aryl groups which may form the substituent designated by $R_7$, $R_8$ and $R_9$ include mononuclear aryl groups such as phenyl or substituted phenyl such as tolyl, xylyl, mesityl, 4-methoxyphenyl, etc. The aryl substituent can be a polynuclear aryl group such as naphthyl, anthryl, phenanthryl, etc.

The reaction between the phosphonate of formula XXVI and the compound of formula XXII can be carried out by first providing a solution of an alkali metal base and the phosphonate of formula XXVI in an inert organic solvent and then adding the compound of formula XXII to this reaction mixture. In carrying out this reaction, any conventional alkali metal base can be utilized, such as the alkali metal hydrides such as sodium hydride and alkyl lithium; alkali metal lower alkoxides such as sodium methoxide and sodium ethoxide; and the alkali metal amide bases such as sodamide, potassium amide, as well as other alkali metal lower alkyl amides. In crrying out this reaction, any conventional inert organic solvent can be utilized such as benzene, toluene, N,N-dimethylformamide, tetrahydrofuran, dioxane, 1,2-dimethoxyethane. In carrying out this reaction, a temperature of from 0° C. to 30° C. may be utilized.

The phosphonate of formula XXVI can be substituted by alkoxy or aryloxy groups. As with $R_7$, $R_8$ and $R_9$ in the phosphorane of formula XXV, the aryl groups denoted by $R_{10}$, and $R_{11}$ in the phosphonate of formula XVI can be mononuclear or polynuclear aryl groups which may be substituted or unsubstituted. When the compound of formula XXVI is substituted by alkoxy groups, it is generally preferred to utilize alkoxy groups containing from 1 to 4 carbon atoms such as methoxy, ethoxy and isopropyl. Among the aryloxy groups, phenoxy groups which are singly or multiply substituted with an alkyl, nitrogen, halogen, lower alkoxy or dialkylamino group are generally preferred.

In the compounds of formulae XXV and XXVI, $RLhd 1'$ can be aryl, aralkyl or alkyl. the alkyl group includes both lower alkyl groups containing from 2 to 6 carbon atoms and higher alkyl groups containing from 7 to 18 carbon atoms. Among the preferred lower alkyl groups are ethyl, propyl, isopropyl, pentyl, butyl, etc. Among the higher alkyl groups are hexadecyl, octadecyl, decyl, tetradecyl, pentadecyl, octyl, etc. the $R_1'$ group utilized in the compound of formula XXV and formula XXVI is converted through to the corresponding groups in the compound of formula I and formula III above.

The stereoconfiguration at the 9-10 double bond in the compound of formula III depends upon the configuration about the double bond in the 2-3 position in the compound of formula XX. Therefore, if the 2-3 double bond in the compound of formula XX is a trans double bond, the configuration about the double bond in the 9-10 position of formula III will be a trans double bond. On the other hand, if the double bond in the 2-3 position in the compound of formula XX is a cis double bond, the configuration about the 9-10 double bond in the compound of formula III will be a cis configuration. On the other hand, if the compound of formula XX contains a mixture of cis and trans isomers, a compound of formula III which is produced thereby is a mixture of cis/trans isomers.

The compound of formula I where R is —CHO is vitamin A aldehyde. Vitamin A aldehyde can be prepared from the compound of formula V where $R_1''$ is hydrogen via an intermediate of the formula:

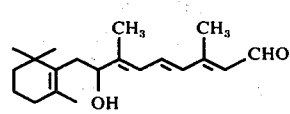

In converting the compound of formula V where $R_1'$ is hydrogen to the compound of formula XIX, the compound of formula III is treated with a selective oxidizing agent such as manganese dioxide, silver carbonate or nickel peroxide. Any of the conditions conventional in utilizing these oxidizing agents can be utilized in carrying out out this conversion.

The compound of formula XIX can be converted to vitamin A aldehyde by treating with a dehydrating agent as described in connection with reaction step (d) hereinabove. However, it may be best before carrying out reaction step (d) to protect the aldehyde group via an acetal derivative and to convert the free hydroxy group to a leaving group. Hence, a compound of the formula:

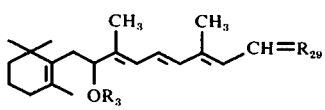

wherein —OR$_3$ is as above; and R$_{29}$ is oxo or an acetalized oxo group.

In forming the compound of formula XIX where —OR$_3$ is a leaving group, the same leaving groups and the same manner of formation described in connection with the formation of compounds of the formula VI can be used. In forming the acetal of formula XIX, any conventional method of acetalizing an oxo group can be utilized. The acetal is generally formed by reaction with a lower alkane diol which contains from 2 to 6 carbon atoms to yield a lower alkylene dioxy at the 15 position. Any conventional acetal protecting group can be utilized to protect the oxo group in the compound of formula XIX, with the lower alkylene dioxy groups, i.c., alkylene dioxy groups containing from 2 to 6 carbon atoms, being preferred.

Where R$_{29}$ in the compound of formula XIX-B is an actual group, the compound of formula XIX when treated with a dehydrating agent as described in connection with reaction step (d), is converted to an acetal of vitamin A aldehyde which has the formula:

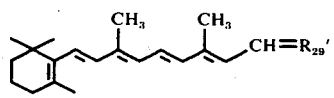

wherein R$_{29}'$ is an acetalized oxo group. The compound of formula XX can be converted to vitamin A aldehyde by any conventional means of hydrolyzing an acetal group.

The following examples are illustrative but not limitative of the invention. In the examples, all temperatures are in degrees centigrade.

EXAMPLE 1

Trans-1-hydroxy-3-methyl-5-(1-hydroxy-2,2,6-trimethylcyclohexyl)-pent-2-en-4yne

To a stirred solution of 18 ml. of etheral ethyl-magnesium bromide (3M) in 30 ml. of tetrahydrofuran was added 5.1 g. of trans-1-hydroxy-3-methyl-pent-2-en-4-yne in 55 ml. of dichloromethane. The mixture was stirred for 2 hours at room temperature and 7.0 g. of 2,2,6-trimethylcyclohexanone in 125 ml. of dichloromethane was added at 0° C. The solution was stirred for 1 hour at room temperature, refluxed for 1½ hours and allowed to stand overnight. The reaction mixture was treated with water until the inorganic salts precipitated. Sodium sulfate was added, the suspension was filtered, and the filtrate concentrated to give a crude yellow oil which was dissolved in diethyl ether, washed with sodium bicarbonate and water, and dried. Evaporation of the ether gave a yellow oil which precipitated 3.2 g. of trans-1-hydroxy-3-methyl-5-(1-hydroxy-2,2,6-trimethylcyclohexyl)-pent-2-en-4-yne as a white crystalline product upon trituration with hexane.

EXAMPLE 2

3-Methyl-5-(1-hydroxy-2,2,6-trimethylcyclohexyl)-pent-2-en-4-yn-1-al

The diol (6.0 g.), trans-1-hydroxy-3-methyl-5(1-hydroxy-2,2,6-trimethylcyclohexyl)-pent-2-en-4-yne, was stirred at room temperature in 400 ml. of dichloromethane with 30 g. of manganese dioxide for 1½ hours. Filtration and evaporation of the solvent afforded 3-methyl-5-(1-hydroxy-2,2,6-trimethylcyclohexyl)-pent-2-en-4-yn-1-al. UV in isopropanol, $\lambda_{max} = 287$ m$\mu$.

EXAMPLE 3

Ethyl 3,7-dimethyl-9-(1-hydroxy-2,2,6-trimethylcyclohexyl)-nona-2,4-trans,6-trien-8-ynoate A solution of 7.45 g. of ethyl-3-diethylphosphonosenecioate in 30 ml. of tetrahydrofuran was added to a suspension of sodium hydride dispersion (1.26 g., 59.2% by weight NaH) in 60 ml. of tetrahydrofuran at 0° C. After the addition, the mixture was stirred for 1 hour and a solution of the aldehyde, 3-methyl-5-(1-hydroxy-2,2,6-trimethylcyclohexyl)-pent-2-en-4-yn-1-al, in 30 ml. of tetrahydrofuran was added at 0° C. The solution was stirred at room temperature for 2 hours and then poured into ice water. The organic layer was washed with brine, dried and concentrated to afford the crude ester, ethyl 3,7-dimetyl-9-(1-hydroxy-2,2,6-trimethylcyclohexyl)-nona-2,4-trans,6-trans-trien-8-ynoate. This crude ester was chromatographed on activity III alumina to give pure ethyl 3,7-dimethyl-9-(1-hydroxy-2,2,6-trimethylcyclohexyl)-nona-2,4-trans,6-trans-trien-8ynoate.

UV in isopropanol, $\lambda_{max} = 332$ m$\mu$]($\epsilon = 40,820$).
IR (film), $\nu_{max} = 3500, 2710$ cm$^{-1}$.

EXAMPLE 4

Ethyl 3,7-dimethyl-8-keto-9-(2,6,6-trimethylcyclohexen-1-yl)-nona-2,4-trans,6-trans-trienoate A xylene solution of 1.0 g. of the hydroxy ester, ethyl 3,7-dimethyl-9-(2-hydroxy-2,2,6-trimethylcyclohexyl)-nona-2,4-trans,6-trans-trien-8-ynoate, was refluxed under argon with 0.36 g. of tris(triphenylsilyl) vanadate, 0.09 g. of triphenylsilanol, and 0.02 g. of benzoic acid for 3 hours. The solution was cooled, concentrated, diluted with hexane, and filtered. The filtrate was washed with bicarbonate and brine and dried. Removal of solvent gave a crude oil which was chromatographd on activity III alumina to give pure ethyl 3,7-dimethyl-8-keto-9-(2,6,6-trimethylcyclohexen-1-yl)-nona-2,4-trans,6-trans-trienoate.

UV in hexane, $\lambda_{max} = 326$ m$\mu$.

EXAMPLE 5

Ethyl 3,7-dimethyl-8-hydroxy-9-(2,6,6-trimethylcyclohexen-1-yl)-nona-2,4-trans,6-trans-trienoate The keto ester (2.2 g.), ethyl 3,7-dimethyl-8-keto-9-(2,6,6-trimethylcyclohexen-1-yl)-nona-2,4-trans,6-trans-trienoate, in 100 ml of ethanol was stirred for 72 hours with 0.6 g. of sodium borohydride. Water was added and the solution concentrated and the residue extracted with diethyl ether. The extracts were washed with water, dried, and concentrated to give ethyl 3,7- dimethyl-8-hydroxy-9-(2,6,6-trimethylcyclohexen-1-yl) -nona-2,4-trans,6-trans-trienoate.

UV is isopropanol, $\lambda_{max} = 312$–3 m$\mu$ ($\epsilon = 26,500$).

EXAMPLE 6

Vitamin A acid ethyl ester

The hydroxy ester (0.35 g.), ethyl 3,7-dimethyl-8-hydroxy-9-(2,6,6-trimethylcyclohexen-1-yl)-nona-2,4-trans,6-trans-trienoate, was dissolved in 1 ml. of dichloromethane and 0.16 ml. of pyridine and the solution was cooled to −5° C. Acetyl chloride (0.1 g.) in 1 ml. of dichloromethane was added and the mixture was stirred for 30 minutes at −5' C. Water was added and the organic phase was washed with dilute sulfuric acid, sodium bicarbonate, and water. Retreatment as described gave a solution of the 8-acetoxy derivative of the hydroxy ester, i.e., ethyl-3,7-dimethyl-8-acetoxy-9-(2,6,6-trimethylcycohexen-1-yl)-nona-2,4-trans,6-trans-trienoate. (Ir $\nu_{max}$ (film) = 1735 cm$^{-1}$). The solution was cooled to −50° C. and stirred vigorously during the rapid addition of 0.165 ml. of precooled 62% by weight aqueous hydrobromic acid (−20° C.). The mixture was stirred 15 minutes at −50° C. and ice water and sodium bicarbonate were added. The dichloromethane solution was washed with water, dried and concentrated to give vitamin A acid ethyl ester.

UV in isopropanol, $\lambda_{max} = 352$ m$\mu$ ($\epsilon = 34,710$).
Ir (film), $\nu_{max} = 1705$ cm$^{-1}$.

EXAMPLE 7

1-Hydroxy-3,7-dimethyl-9-(1-hydroxy-2,2,6-trimethylcyclohexyl)-nona-2,4,6-trans-trien-8-yne The hydroxy ester (0.5 g.), ethyl 3,7-dimethyl-9-(1-hydroxy-2,2,6-trimethylcyclohexyl)-nona-2,4,6-trans-trien-8-ynoate, in 18 ml. of anhydrous diethyl ether was added to a suspension of 0.88 g. of lithium aluminum hydride in 18 ml. of diethyl ether at −70° C. The mixture was stirred for 1½ hours and then decomposed with saturated aqueous sodium sulfate solution. The mixture was filtered and the ether evaporated to give 1-hydroxy-3,7-dimethyl-9-(1-hydroxy-2,2,6-trimethylcyclohexyl)-nona-2,4,6-trans-trien-8-yne.

UV in ethanol, $\lambda_{max} = 303$ m$\mu$ ($\epsilon = 36,535$).

EXAMPLE 8

1-Acetoxy-3,7-dimethyl-9-(1-hydroxy-2,2,6-trimethylcyclohexyl)-nona-2,4,6-trans-trien-8-yne Acetic anhydride (0.2 ml.) was added to a solution of 0.15 g. of the diol, 1-hydroxy-3,7-dimethyl-9-(1-hydroxy-2,2,6-trimethylcycohexyl)-nona-2,4,6-trans-trien-8-yne in 5 ml. of pyridine. The solution was heated to 50°–60° C for 1½ hours and poured into ice water and extracted with diethyl ether. The extracts were washed with sodium bicarbonate, saturated aqueous cupric sulfate, and brine and dried to give 1-acetoxy-3,7-dimethyl-9-(1-hydroxy-2,2,6-trimethylcyclohexyl)-nona-2,4,6-trans-trien-8-yne.

UV is isopropanol, $\lambda_{max} = 305$ m$\mu$.

EXAMPLE 9

1-Acetoxy-3,7-dimethyl-8keto-9-(2,6,6-trimethylcyclohexen-1-yl)-nona-2,4,6trans-triene A solution of 1.30 g. of the acetylenic acetate, 1-acetoxy-3,7-dimethyl-9-(1-hydroxy-2,2,6-trimethylcyclohexyl)-nona-2,4,6-trans-trien-8-yne, 0.47 g. of tris(-triphenylsilyl) vanadate, 0.12 g. of triphenylsilanol, 0.3 g. of benzoic acid, and 0.03 g. of hydroquinone in 25 ml. of xylene was refluxed under argon for 2 hours. The solvent was evaporated and the residue triturated with hexane and cooled and filtered. Evaporation of the hexane afforded crude 1-acetoxy-3,7-dimethyl-8-keto-9-(2,6,6-trimethylcyclohexen-1-yl)-nona-2,4,6-trans-triene which was chromatographed on silica gel to afford the pure 1-acetoxy-3,7-dimethyl-8-keto-9-(2,6,6-trimethylcyclohexen-1-yl)-nona-2,4,6-trans-triene.

UV in ethanol, $\lambda_{max} = 313$ m$\mu$ ($\epsilon = 26,005$).

EXAMPLE 10

1-Acetoxy-3,7-dimethyl-9-(1-hydroxy-2,2,6-trimethylcylcohexyl)-nona-2,4-trans,6-cis-trien-8-yne A solution of 11.78 g. of the diol 7-hydroxy-3,7-dimethyl-9-(2-hydroxy-2,2,6-trimethylcylcohexyl)-nona-1,3,5-trien-8-yne, in 33 ml. of glacial acetic acid was warmed to 40° C for 2 hours. The reaction mixture was poured into 300 ml. of ice water and extracted with diethyl ether. The extracts were washed with brine, sodium bicarbonate, and brine and dried. Evaporation of the solvent gave 1-acetoxy-3,7-dimethyl-9-(1-hydroxy-2,2,6-trimethylcyclohexyl)-nona-2,4-trans,6-cis-trien-8-yne. UV in ethanol, $\lambda_{max} = 302$ m $\mu$

EXAMPLE 11

3-Hydroxy-3,7-dimethyl-nona-4,6,8-triene-1-yne

A solution of ethyl bromide (5.45 g.) in tetrahydrofuran was added to a suspension of magnesium (1.20 g.) in tetrahydrofuran and the mixture was refluxed for 30 minutes. Acetylene was bubbled into the solution for 2 hours at room temperature and a solution of 6-methyl-octa-3,5,7-trien-2-one (1.80 g.) in tetrahydrofuran was added. The mixture was stirred at room temperature for 1½ hours and poured into saturated ammonium chloride solution. The organic layer was washed with brine and dried. Evaporation of the solvent gave 3-hydroxy-3,7-dimethyl-nona-4,6,8-trien-1-yne which was chromatographed on activity III alumina to give of pure 3-hydroxy-3,7-dimethyl-nona-4,6,8-trien-1-yne.

UV in isopropanol, $\lambda_{max} = 267$ m$\mu$ ($\epsilon = 30,225$).

EXAMPLE 12

7-hydroxy-3,7-dimethyl-9-(1-hydroxy-2,2,6-trimethylcyclohexyl)-nona-1,3,5-trien-8-yne A solution of ethyl bromide (1.75 g.) in diethyl ether was added to a suspension of magnesium (0.385 g.) in ether and the mixture was heated to reflux for 30 minutes. A solution of the alcohol, 3-hydroxy-3,7-dimethyl-nona-4,6,8-trien-1-yne, (1.0 g.) in dry benzene was added and the mixture refluxed 30 minutes. A solution of 2,2,6-trimethylcyclohexanone (1.12 g.) in benzene was added and the mixture refluxed for 15 minutes and poured into saturated aqueous ammonium chloride solution. The organic phase was washed with brine dried and concentrated to give 7-hydroxy-3,7-dimethyl-9-(1-hydroxy-2,2,6-trimethylcyclohexyl)-nona-1,3,5-trien-8-yne which was chromatographed on activity III alumina to give pure 7-hydroxy-3,7-dimethyl-9-(1-hydroxy-2,2,6-trimethylcycohexyl)-nona-1,3,5-trien-8-yne.

UV in isopropanol, $_{max} = 268$–9 m$\mu$]($\epsilon = 30,535$)

EXAMPLE 13

1-Acetoxy-3,7-dimethyl-9-(1-hydroxy-2,2,6-trimethylcyclohexyl)-nona-2,4-trans,6-cis-trien-8-yne A solution of 1.33 g. of the diol, 7-hydroxy-3,7-dimethyl-9-(1-hydroxy-2,2,6-trimethylcyclohexyl)-nona-1,3,5-trien-8-yne, 1.33 g. of glacial acetic acid, and 8 ml. of benzene was refluxed under argon for 4 hours. The solution was poured into water and extracted with diethyl ether. The extracts were washed with sodium bicarbonate and brine and dried. Evaporation of the solvents afforded 1-acetoxy-3,7-dimethyl-9-(1-hydroxy-2,2,6-trimethylcyclohexyl)-nona-2,4-trans,6-cis-trien-8-yne.

UV in isopropanol, $\lambda_{max} = 302$ m$\mu$ ($\epsilon = 30,700$)

EXAMPLE 14

3-Hydroxy-3,7-dimethyl-9-(1-hydroxy-2,2,6-trimethylcyclohexyl)-nona-1,4,6-cis/trans-trien-8-yne To a stirred solution of vinylmagnesium chloride (6.5 ml. 2.9M) in 25 ml of tetrahydrofuran was added 2.0 g of the ketone, 2-keto-6-methyl-8-(1-hydroxy-2,2,6-trimethylcyclohexyl)-octa-3,5-cis/trans-dien-7-yne, in 45 ml of tetrahydrofuran. The mixture was refluxed for 1 hour and saturated aqueous magnesium sulfate was added. The mixture was filtered and the filtrate concentrated to afford 3-hydroxy-3,7-dimethyl-9-(1-hydroxy-2,2,6-trimethylcyclohexyl)-nona-1,4,6-cis/-trans-trien-8-yne. This product was chromatographed on activity III alumina to afford pure product.

UV in isopropanol $\lambda_{max} = 270$ m$\mu$ ($\epsilon = 23,510$)
Ir (film), $\nu_{max} = 3450$ cm$^{-1}$

EXAMPLE 15

1-Acetoxy-3,7-dimethyl-9-(1-hydroxy-2,2,6-trimethylcyclohexyl)-nona-2,4,6-cis/trans-trien-8-yne.

The diol (0.59 g.), 3-hydroxy-3,7-dimethyl-9-(1-hydroxy-2,2,6-trimethylcyclohexyl)-nona-1,4,6-cis/-trans-trien-8-yne, was heated at 40° C for 1 hour with 5 ml. of glacial acetic acid. The mixture was poured onto ice water, extracted with diethyl ether, and the extracts were washed with sodium bicarbonate and brine and dried. Removal of the solvent afforded 1-acetoxy-3,7-dimethyl-9-(1-hydroxy-2,2,6-trimethylcyclohexyl)-nona-2,4,6-cis/trans-trien-8-yne.

UV in isopropanol $\lambda_{max} = 303$ m$\mu$

EXAMPLE 16

1-Acetoxy-3,7-dimethyl-8-keto-9-(2,6,6-trimethylcyclohexen-1-yl)-nona-2,4,6-triene A solution of 11.4 g. of the acetoxy acetylenic alcohol, 1-acetoxy-3,7-dimethyl-9-(1-hydroxy-2,2,6-trimethylcyclohexyl)-nona-2,4-trans,6-cis-trien-8-yne, 3.59 g. of tris(triphenylsilyl) vanadate, 0.93 g. of triphenylsilanol, and 0.22 g. of benzoic acid was heated to reflux in 200 ml. of xylene for 3 hours. The solvent was removed and the residue was triturated with hexane, cooled and filtered. The filtrate was concentrated to give 13.6 g. of a crude oil. A 10.6 g. portion was chromatographed on deactivated silica gel to give 1-acetoxy-3,7-dimethyl-8-keto-9-(2,6,6-trimethylcyclohexen-1-yl)-nona-2,4-trans,6-cis/trans-triene.

UV in isopropanol, $\lambda_{max} = 310$ m$\mu$

EXAMPLE 17

By the procedure of Example 16, a solution of 1.0 g. of 1-acetoxy-3,7-dimethyl-9-(1-hydroxy-2,2,6-trimethylcyclohexyl)-nona-2,4,6-cis-trien-8-yn and 0.2 g. of tris(triphenylsilyl) vanadate in xylene was heated to reflux for 2 hours to give 1-acetoxy-3,7-dimethyl-8-keto-9-(2,6,6-trimethylcyclohexen-1-yl)-nona-2,4,6-cis/trans-triene.

UV in isopropanol: 1:1 ratio of $\lambda_{max} = 302$ m$\mu$ (starting material) and $\lambda_{max} = 310$ m$\mu$.

EXAMPLE 18

By the procedure of Example 16, a solution of 1.0 g. of 1-acetoxy-3,7-dimethyl-9-(2,2,6-trimethylcyclohexyl)-nona-2,4,6-cis-trien-8-yne, 0.3 g. of tris(triphenylsilyl) vanadate, 0.09 g. of triphenylsilanol, and 0.015 g. of benzoic acid was refluxed in 15 ml. of mesitylene for 1¾ hours. Isolation of the product as described above gave 1.2 g. of crude oil which afforded pure 1-acetoxy-3,7-dimethyl-8-keto-9-(1-hydroxy-2,6,6-trimethylcyclohexen-1-yl)-nona-2,4,6-cis/trans-triene after chromatography on deactivated silica gel.

UV in isopropanol, $\lambda_{max} = 310$ m$\mu$.

EXAMPLE 19

A solution of 1.30 g. of 1-acetoxy-3,7-dimethyl-9-(1-hydroxy-2,2,6-trimethylcyclohexyl)-nona-2,4,6-trans-trien-8-yne, 0.47 g. of tris (triphenylsilyl) vanadate, 0.118 g. of triphenylsilanol, 0.025 g. of benzoic acid, and 0.005 g. of hydroquinone was refluxed in 25 ml. of xylene for 2 hours. Isolation of the crude product afforded 1.25 g. of crude oil which was chromatographed as described in Example 15 to afford 1-acetoxy-3,7-dimethyl-8-keto-9-(2,6,6-trimethylcyclohexen-1-yl)-nona-2,4,6-trans-triene.

UV in isopropanol, $\lambda_{max} = 311-312$ m$\mu$.

EXAMPLE 20

A solution of 0.43 g. of 1-acetoxy-3,7-dimethyl-9-(1-hydroxy-2,2,6-trimethylcyclohexyl)-nona-2,4,6-cis-trien-8-yne in 6.5 ml. of xylene was heated to reflux for 1¼ hours with 0.4 g. of the catalytic solids precipitated from a previous rearrangement reaction which used tris (triphenylsilyl) vanadate, triphenylsilanol, benzoic acid, and hydroquinone as described in Example 18. Isolation afforded crude product which was chromatographed to give pure 1-acetoxy-3,7-dimethyl-8-keto-9-(2,6,6-trimethylcyclohexen-1-yl)-nona-2,4,6-cis/trans-triene.

UV in isopropanol, $\lambda_{max} = 310$ m$\mu$.

EXAMPLE 21

Isomerization of 1-acetoxy-3,7-dimethyl-8-deto-9-(2,6,6-trimethylcyclohexen-1-yl)-nona-2,4,6-triene A solution of 78 mg. of the ketoacetate, 1-acetoxy-3,7-dimethyl-8-keto-9-(2,6,6-trimethylcyclohexen-1-yl)-nona-2,4,6-cis/trans-triene (mainly having a cis configuration at the 6,7-double bond), in 0.5 ml. of glacial acetic acid was allowed to stand at room temperature for 20 hours. The solution was poured into water and extracted with diethyl ether. The combined extracts were washed successively with sodium bicarbonate and brine and dried. Removal of the solvent afforded the compound 1-acetoxy-3,7-dimethyl-8-keto-9-(2,6,6-trimethylcyclohexen-1-yl)-nona-2,4,6-triene which was reduced in the cis configuration about the 6,7-double bond.

Nmr: $\delta_{CDCl_3}^{TMS}$ (C-9 methylene) = 3.25 (6-cis) and 3.42 ppm (6-trans).

EXAMPLE 22

A solution of 4.0 g. of acetoxy ketone, 1-acetoxy-3,7-dimethyl-8-keto-9-(2,6,6-trimethylcyclohexen-1-yl)-nona-2,4-trans,6-cis/trans-triene, and 26.5 g. of piperidine acetate in 400 ml. of benzene was refluxed for 90 hours under argon. Water and diethyl ether were added and the mixture was extracted with diethyl ether. The extracts were washed with 10% by weight aqueous HCl, sodium bicarbonate, and brine and dried. Removal of the solvent gave 4.0 g. of crude product which was chromatographed on silica gel to give the all trans acetoxy ketone.

UV in isopropanol, $\lambda_{max} = 310$ m$\mu$ ($\epsilon = 32,640$).
Ir: $\nu_{max}$ (film) 1735, 1660, and 1265 cm$^{-1}$.
Nmr: $\delta_{CDCl}$ $^{TMS}$ (C-9 methylene) = 3.42 ppm.

EXAMPLE 23

The following isomerizations of the acetoxy ketone of Example 21 were carried out. In this example, the acetoxy ketone was a 6-cis/trans isomeric mixture. In the isomerized product there was a substantial increase in the trans configuration about the 6–7 double bond. In this example, the steps of extraction and isomerization were carried out in the same manner as in Example 21.

a. Starting with 0.12 g. acetoxy ketone (6-cis/trans), 0.093 g. tetramethylammonium acetate, and refluxed in acetone 20 hours.

b. Starting with 0.12 g. acetoxy ketone (6-cis/trans), 0.0193 g. tetramethylammonium acetate, and refluxed in diethyl ketone 20 hours.

c. Starting with 0.115 g. acetoxy ketone (6-cis/trans), 0.076 g. diazabicyclo [2.2.2] octane, and refluxed 5 hours in diethyl ketone.

d. Starting with 0.06 g. acetoxy ketone (6-cis/trans), 1.0 ml. pyridine and heated at reflux for 7 hours.

e. Starting with 0.10 g. acetoxy ketone (6-cis/trans), 1.5 ml. pyridine and heated to reflux for 105 hours.

EXAMPLE 24

All trans-1,8-dihydroxy-3,7-dimethyl-9-(2,6,6-trimethylcyclohexen-1-yl)-nona-2,4,6-triene 1.765 g. of the keto acetate, all trans-1-acetoxy-3,7-dimethyl-8-keto-9-(2,6,6-trimethylcyclohexen-1-yl)-nona-2,4,6-triene in 80 ml. of ethanol was stirred for 90 hours with 0.97 g. of sodium borohydride. Water was added to decompose the excess hydride and the mixture was filtered. The filtrate was concentrated and redissolved in diethyl ether. The ether solution was washed with brine and dried. The solvent was removed to give all-trans-1,8-dihydroxy-3,7-dimethyl-9-(2,6,6-trimethylcyclohexene-1-yl)-nona-2,4,6-triene.

UV in isopropanol $\lambda_{max} = 280$ m$\mu$.

EXAMPLE 25

All trans-1,8-diacetoxy-3,7-dimethyl-9-(2,6,6-trimethylcyclohexen-1-yl)-nona-2,4,6-triene A solution of 0.9 g. of the diol, all-trans-1,8-dihydroxy-3,7-dimethyl-9-(2,6,6-trimethylcyclohexen-1-yl)-nona-2,4,6-triene in 20 ml. of pyridine was stirred at room temperature with 1 ml. of acetic anhydride for 18 hours and the mixture was poured into ice water and diethyl ether. The organic layer was washed with sodium bicarbonate, saturated aqueous cupric sulfate, and brine and dried. Evaporation of the solvent gave 0.85 g. of all trans-1,8-diacetoxy-3,7-dimethyl-9-(2,6,6-trimethylcyclohexen-1-yl)-nona-2,4,6-triene.

UV in isopropanol $\lambda_{max} = 280$ m$\mu$.
Ir (film) $\nu_{max} = 1730$ and 1230 cm$^{-1}$.

EXAMPLE 26

Vitamin A acetate

A solution of 0.445 g. of the diacetate, all-trans-1,8-diacetoxy-3,7-dimethyl-9-(2,6,6-trimethylcyclohexen-1-yl)-nona-2,4,6-triene, in 10 ml. of dichloromethane was stirred at −50° C. and 1.0 ml. of 62% by weight aqueous hydrobromic acid (−20° C) was added. The mixture was stirred at −50° C. for 7 minutes and then 10 ml. of ice water, 10 ml. of dichloromethane and a solution of 1.7 g. of sodium carbonate in 10 ml. of water was added. The mixture was stirred in an ice bath for 2½ hours and the organic layer was washed with brine and dried. Evaporation of the solvent afforded 0.4 g. of crude product which was purified by chromatography on silica gel containing 20% sodium acetate to give 0.155 g. of all trans vitamin A acetate.

UV in isopropanol $\lambda_{max} = 327$ m$\mu$ ($\epsilon = 39,000$).

EXAMPLE 27

A solution of 0.1 g. of all trans 1,8-dihydroxy-3,7-dimethyl-9-(2,6,6-trimethylcyclohexen-1-yl)-nona-2,4,6-triene was oxidized with 0.5 g. of activated manganese dioxide in 5 ml. of dichoromethane to produce all trans 3,7-dimethyl-8-hydroxy-9-(2,6,6-trimethylcyclohexen-1-yl)-nona-2,4,6-trien-1-al.

EXAMPLE 28

To a solution of 200 mg. of phosphorous oxychloride in 10 ml. of pyridine was added 300 mg. of the hydroxyaldehyde, all trans-3,7-dimethyl-8-hydroxy-9-(2,6,6-trimethylcyclohexen-1-yl)-nona-2,4,6-trien-1-al, in 2 ml. of pyridine. The mixture was stirred at room temperature for 3 hours, poured into ice water, and extracted with diethyl ether. The extracts were washed with saturated aqueous sodium bicarbonate solution, saturated aqueous cupric sulfate, and brine, and dried. Evaporation of the solvent afforded vitamin A aldehyde.

EXAMPLE 29

1-Acetoxy-3,7-dimethyl-8-keto-9-(2,6,6-trimethylcyclohexen-1-yl)-nona2,4,6-triene and 1-acetoxy-3,7-dimethyl-8-keto-9-(2,6,6-trimethylcyclohexylidene)-nona-2,4,6-triene.

A solution of 0.166 g. of 1-acetoxy-3,7-dimethyl-9-(1-hydroxy2,2,6-trimethylicyclohexyl-nona-2,4-trans, 6-cis-trien-8-yne and 0.004 g. of hydroquinone in 1.0 ml. of benzene was heated under argon at reflux with 0.031 g. of crude tris(3-nitrophenylsilyl)vandate for 1 hours. The solution was cooled, diluted with hexane, and chilled to permit precipitation of the catalyst. The mixture was filtered and the filtrate concentrated at reduced pressure to afford 0.135 g. of a mixture (about 1:1 parts by weight) of 1-acetoxy-3,7-dimethyl-8-keto-9-(2,6,6-trimethylcyclohexen-1-yl)-nona-2,4,6-triene and 1-acetoxy-3,7-dimethyl-8-keto-9-(2,2,6-trimethylcyclohexylidenyl)-nona-2,4,6-triene.

EXAMPLE 30

By the procedure of Example 29, a solution of 0.160 g. of 1-acetoxy-3,7-dimethyl-9-(1-hydroxy-2,2,6-trimethylcyclohexyl)-nona2,4-trans-6-cis-trien-8-yne in 1.0 ml. of toluene containing 0.004 g. of hydroquinone was heated to 80°–82° C. for one hour with 0.040 g. of crude tris-(3,5-dinitrophenylsilyl)vandate. The solution was diluted with hexane and chilled. The catalyst was removed by filtration and the filtrate concentrated to give 0.110 g. of 1-acetoxy-3,7-dimethyl-8-keto-9-(2,6,6-trimethylcyclohexen-1-yl)-nona-2,4,6-triene and 1-acetoxy-3,7-dimethyl-8-keto-9-(2,2,6-trimethyl-cyclohexylidenyl)-nona-2,4,6-triene.

EXAMPLE 31

A solution of 0.11 g. of the mixture produced in Example 30 in 1 ml. of toluene was added to a mixture of 0.40 g. of piperidine and 0.144 g. of glacial acetic acid in 4 ml. of toluene and was refluxed for 8 hours. The mixture was diluted with diethyl ether, washed with water, sodium bicarbonate solution, 2N hydrochloric acid, and brine and dried. Evaporation of the organic solution afforded a mixture of 1-acetoxy-3,7-dimethyl-8-keto-9-(2,6,6-trimethylcyclohexen-1-yl)-nona-2,4,6-triene in which the amount of the 6-cis isomer was reduced and 1-acetoxy-3,7-dimethyl-8-keto-9-(2,2,6-trimethylcyclohexylidenyl)-nona-2,4,6-triene.

EXAMPLE 32

By the method of Example 24, to a solution of 0.10 g. of the mixture produced in Example 31, in 10 ml. of ethanol is added 0.25 g. of sodium borohydride. After stirring at room temperature for 90 hours, the mixture is poured into ice water and 0.2N hydrochloric acid and extracted with diethyl ether. The extracts are washed with aqueous sodium bicarbonate and brine and dried. Evaporation of the solvent affords a mixture of the diols 1,8-dihydroxy-3,7-dimethyl-9-(2,6,6-trimethylcyclohexen-1-yl)-nona-2,4-trans,6-trans-triene and 1,8-dihydroxyl-3,7-dimethyl-9-(2,2,6-trimethylcyclohexylidenyl)-nona-2,4,6-triene.

EXAMPLE 33

By the method of Example 25, the mixture of diols from Example 32 (0.08 g.) is acetylated using 2.0 ml. of pyridine and 0.2 ml. of acetic anhydride. The crude product is isolated as in Example 25 giving a mixture of diacetates, 1,8-diacetoxy-3,7-dimethyl-9-(2,6,6-trimethylcyclohexen-1-yl)-nona-2,4-trans,6-trans-triene and 1,8-diacetoxy-3,7-dimethyl-9-(2,2,4-trimethylcyclohexylideneyl)-nona-2,4,6-triene.

EXAMPLE 34

By the method of Example 26, a solution of 0.82 g. of the diacetoxy compounds produced in Example 33 is treated in 2 ml. of dichloromethane at −50° C. with 0.2 ml. of 62% by weight aqueous hydrobromic acid. Isolation as described in Example 26 affords vitamin A acetate.

EXAMPLE 35

To a solution of 0.038 g. of perfluorotriphenylsilanol was added 0.48 ml. of 1.26% by weight xylene solution of tri n-propyl vanadate. To this solution was added a solution of 1-acetoxy-3,7-dimethyl-9-(1-hydroxy-2,2,6-trimethylcyclohexyl)-nona-2,4-trans, 6-cis-trien-8-yne in 0.52 ml. of xylene. The solution was heated at 80° C. for 25 minutes and then at 100° C. for 40 minutes. The solution was cooled, diluted with hexane, chilled and filtered to remove the catalyst. The filtrate was washed with water, dried and concentrated to afford 0.143 g. of crude 1-acetoxy-3,7-dimethyl-8-keto-9-(2,6,6-trimethylcyclohexen-1-yl)-nona-2,4,6-triene.

EXAMPLE 36

A solution of 0.165 g. of 1-acetoxy-3,7-dimethyl-9-(1-hydroxy-2,2,6-trimethylcyclohexyl)-nona-2,4-trans,6-cis-trien-8-yne, 0.03 g. of tri-pchlorophenylsilanol, 0.24 ml. of 1.26% by weight tri-n-propyl vandate in xylene, 0.003 g. of hydroquinone, and 0.001 g. of hydroquinone in 1.0 ml. of xylene was heated at 110° C. for 40 minutes. Isolation of the product was carried out by first adding hexane. The resulting mixture was chilled and filtered and the filtrate washed with aqueous sodium bicarbonate solution and water and dried. Evaporation of the solvents gave 0.150 g. of 1-acetoxy3,7-dimethyl-8-keto-9-(2,6,6-trimethylcyclohexen-1yl)-nona-2,4,6-triene.

EXAMPLE 37

A solution of 0.186 g. of 1-acetoxy-3,7-dimethyl-9-(1-hydroxy-2,2,6-trimethylcyclohexyl)-2,4-trans,6-cis-trien-8-yne, 0.038 g. of tris(p-trifluoromethylphenyl)-silanol, 0.0061 g. of tri-n-propyl vanadate, 0.006 g. of hydroquinone and 0.002 . of benzoic acid in 1 ml. of toluene was heated to 100° C. for 35 minutes. Isolation as in Example 36 affords 0.322 g. of a mixture of crude 1-acetoxy-3,7-dimethyl-8-keto-9-(2,6,6-trimethylcyclohexen-1-yl)-nona-2,4,6-triene and 1-acetoxy-3,7-dimethyl-8-keto-9-(2,2,6-trimethylcyclohexylidenyl)-nona-2,4,6-triene.

EXAMPLE 38

A solution of 0.330 g. of 1-acetoxy-3,7-dimethyl-9-(1-hydroxy-2,2,6trimethylcyclohexyl)-nona-2,4-trans,6-cis-trien-8-yne, 0.094 g. of tri(m-trifluoromethylphenyl)silanol, 0.012 g. of tri-n-propyl vanadate, 0.006 g. of hydroquinone, and 0.002 g. of benzoic acid in 1.75 ml. of toluene was heated at 100° C. for 35 minutes. Isolationn of the product as in Example 36 gave 0.308 g. of a mixture of crude 1-acetoxy-3,7-dimethyl-8-keto-9-(2,6,6-trimethylcyclohexene-1-yl)-nona-2,4,6-triene and 1-acetoxy-3,7-dimethyl-8-keto-9-(2,2,6-trimethylcyclohexylidenyl)-nona-2,4,6-triene.

EXAMPLE 39

A solution of 0.160 g. of 1-acetoxy-3,7-dimethyl-9-(1-hydroxy-2,2,6-trimethylcyclohexyl)-nona-2,4-trans, 6-cis-trien-8-yne, 0.0225 g. of tri-m-tolylsilanol, 0.24 ml. of 1.26% by weight n-propyl vandate in xylene, 0.003 g. of hydroquinone, and 0.001 g. of benzoic acid in 1 ml. of xylene was refluxed for 50 minutes. Isolation as described in Example 36 affords 0.145 g. of 1-acetoxy-3,7-dimethyl-8-keto-9-(2,6,6-trimethylcyclohexen-1-yl)-nona-2,4,6-triene.

EXAMPLE 40

A solution of 0.181 g. of 1-acetoxy-3,7-dimethyl-9-(1-hydroxy-2,2,6-trimethylcyclohexyl)-nona-2,4-trans,6-cis-trien-8-yne, 0.0185 g. of dicyclohexylmethylsilanol, 0.24 ml. of 1.26% by weight tri-n-propyl vanadate in xylene, 0.003 g. of hydroquinone, and 0.001 g. of benzoic acid in 1 ml. of xylene was refluxed for 5 hours. Isolation as described in Example 36 affords 0.167 g. of crude 1-acetoxy-3,7-dimethyl-8-keto-9-(2,6,6-trimethylcyclohexen-1-yl)-nona-2,4,6-triene.

EXAMPLE 41

A solution of 0.482 g. of 1-acetoxy-3,7-dimethyl-9-(1-hydroxy2,2,6-trimethylcyclohexyl)-nona-2-4-trans,6-cis-trien-8-yne, 0.124 g. of tri-1-naphthylsilanol, 0.018 g. of tri-n-propyl vanadate, 0.007 g. of hydroquinone and 0.003 g. of benzoic acid in 2.3 ml. of xylene was refluxed for one hour. An aliquot was removed and the product examined by UV and nmr. The UV had a broad maximum at $\lambda_{max} = 296-318$ m $\mu$, and the nmr had several additional strong resonances attributable to the initially formed 1-acetoxy-3,7-dimethyl-8-keto-9-(2,2,6-trimethylcyclohexylidenyl)-nona-2,4,6-trien. The major portion of the reaction mixture was refluxed a total of 2.25 hours and the product isolated as described in Example 36 giving a total of 0.434 g. of 1-acetoxy-3,7-dimethyl-8-keto-9-(2,6,6-trimethylcyclohexen-1-yl)-nona-2,4,6-triene having a UV in isopropanol at $\lambda_{max} = 310$ M$\mu$ ($\epsilon = 13,255$). The additional resonances due to the initially formed alpha,beta-unsaturated ketone seen in the aliquot were weak or non-existent.

EXAMPLE 42

A solution of 0.355 g. of 1-acetoxy-3,7-dimethyl-9-(1-hydroxy-2,2,6-trimethylcyclohexyl)-nona-2,4-trans,6-cis-trien-8-yne, 0.054 g. of tri-ptolylsilanol, 0.012 . of tri-n-propyl vanadate, 0.006 g. of hydroquinone, and 0.002 g. of benzoic acid in 1.75 ml. of xylene was refluxed for 2.75 hours. Isolation as described in Example 36 afforded 0.36 g. of crude 1-acetoxy-3,7-dimethyl-8-keto-9-(2,6,6-trimethylcyclohexen-1-yl)-nona-2,4,6-triene.

EXAMPLE 43

A solution of 0.340 g. of 1-acetoxy-3,7-dimethyl-9-(1-hydroxy-2,2,6-trimethylcyclohexyl)-nona-2,4-trans,6-cis-trien-8-yne, 0.053 g. of tricyclohexylsilanol, 0.012 g. of tri-n-propyl vandate, 0.006 g. of hydroquinone and 0.002 g. of benzoic acid in 1.75 ml. of xylene was refluxed for 13 hours. Isolation as described in Example 36 affords 0.269 g. of crude 1-acetoxy-3,7-dimethyl-8-keto-9-(2,6,6-trimethylcyclohexen-1-yl)-nona-2,4,6-triene.

EXAMPLE 44

A solution of 0.347 g. of 1-acetoxy-3,7-dimethyl-9-(1-hydroxy2,2,6-trimethylcyclohexyl-nona-2,4-trans,6-cis-trien-8-yne, 0.042 g. of diphenylmethylsilanol, 0.012 g. of tri-n-propyl vanadate, 0.006 g. of hydroquinone, and 0.003 g. of benzoic acid in 1.75 ml. of xylene was refluxed for 4 hours. Isolation of the product as described in Example 36 affords 0.336 g. of crude 1-acetoxy-3,7-dimethyl-8-keto-9-(2,6,6-trimethylcyclohexen-1-yl)-nona-2,4,6-triene.

EXAMPLE 45

A solution of 0.495 g. of 1-acetoxy-3,7-dimethyl-9-(1-hydroxy-2,2,6-trimethylcyclohexyl)-nona-2,4-trans,6-cis-trien-8-yne, 0.0674 g. of tris(trimethylsilyl)-vanadate, and 0.011 g. of benzoic acid in 2.5 ml. of xylene was refluxed for 3 hours. The mixture was cooled, diluted with diethyl ether, washed with aqueous sodium bicarbonate and water and dried. Evaporation of the solvents affords 0.470 g. of crude 1-acetoxy-3,7-dimethyl-8-keto-9-(2,6,6-trimethylcyclohexen-1-yl)-nona-2,4,6-triene.

EXAMPLE 46

A solution of 0.324 g. of 1-acetoxy-3,7-dimethyl-9-(1-hydroxy-2,2,6-trimethylcyclohexyl)-nona-2,4-trans,6-cis-trien-8-yne, 0.063 g. of tri-pfluorophenyl-silanol, 0.012 g. of tri-n-propyl vanadate, 0.006 g. of hydroquinone, and 0.002 g. of benzoic acid in 1.75 ml. of xylene was heated to 130° C. for one hour. Isolation of the product as described in Example 36 gave 0.312 g. of crude 1-acetoxy-3,7-dimethyl-8-keto-9-(2,6,6-trimethylcyclohexen-1-yl)-nona-2,4,6-triene.

EXAMPLE 47

A solution of 0.371 g. of 1-acetoxy-3,7-dimethyl-9-(1-hydroxy-2,2,6-trimethylcyclohexyl)-nona-2,4-trans,6-cis-trien-8-yne, 0.107 g. of tri-p-bromophenylsilanol, 0.012 g. of tri-n-propyl vanadate, 0.006 g. of hydroquinone, and 0.002 g. of benzoic acid in 1.75 ml. of toluene was refluxed for 35 minutes. Isolation as in Example 36 affords 0.293 g. of a mixture of crude 1-acetoxy-3,7-dimethyl-8-keto-9-(2,6,6-trimethylcyclohexen-1-yl)-nona-2,4,6-triene and 1-acetoxy-3,7-dimethyl-8-keto-9-(2,2,6-trimethylcyclohexylidenyl)-nona-2,4,6-triene.

EXAMPLE 48

Preparation of tris(3,5-dinitrophenyl)silanol

To a stirred mixture of 15.41 g. of nitronium tetrafluoroborate and 95 ml. of tetramethylene sulfone was added at 15°-25° C. over 20 minutes 10.8 g. of triphenylsilanol. The solution was heated to 35° C. for 15° C. and treated with a second portion of 16.88 g. of nitronium tetrafluoroborate. The temperature was increased to 95° C. and the mixture stirred at 95° C. for 1⅓ hour. The mixture was cooled, pured onto ice and saturated aqueous sodium bicarbonate and was extracted with diethyl ether. The extracts were washed with brine, dried, and concentrated to give 20.13 g. of a yellow powder, tris(3,5-dinitrophenyl)silanol.

EXAMPLE 49

Preparation of tris (3,5-dinitrophenylsilyl)vanadate

To a solution of 0.44 g. of tri-n-propyl vanadate in 2.0 ml. of dioxane was added a solution of tris(3,5-dinitrophenyl)silanol (0.204 g.) in 3.0 ml. of dioxane. The mixture was stirred over activated 5A molecular sieves for 40 minutes at 25° C. and 80° C. for two hours. An aadditional 0.011 g. of n-propyl vanadate was then added and the mixture was stirred at 80° C. for 7 hours, cooled, decanted from the molecular sieves, and diluted with hexane. A precipitate formed and was collected by filtration to give 0.130 g. of tris(3,5-dinitrophenylsilyl)vanadate

EXAMPLE 50

Preparation of tris(3-nitrophenyl)silanol

To a solution of 1.41 g. of triphenylsilanol in 7 ml. of tetramethylene sulfone at 10° C. was added 2.50 g. of nitronium tetrafluoroborate in 30 ml. of tetramethylene sulfone over 30 minutes at 10°-20° C. The mixture was stirred at 10°-20° C. for 25 minutes, poured into 100 ml. of saturated sodium bicarbonate solution and was extracted with diethyl ether. The extracts were washed with brine, dried, and concentrated to give 1.95 g. of crude tris(3-nitrophenyl)silanol.

EXAMPLE 51

Preparation of tris(3-nitrophenylsilyl)vanadate

To a solution of 0.254 g. of tris(3-nitrophenyl)silanol in 10 ml. of benzene was added 0.055 g. of tri-n-propyl vanadate. The mixture was stirred at 25° C. for 10 minutes and then heated to reflux for 40 minutes after which time 7 ml. of the benzene was distilled out. Toluene (15 ml.) was added and 9 ml. distilled out over 30 minutes. The reaction mixture was then diluted with 100 ml. of hexane, chilled overnight, and filtered to afford 0.237 g. of tris(3-nitrophenylsilyl)vanadate.

EXAMPLE 52

This example is directed to the preparation of different catalysts that can be utilized in place to the tris (triphenylsilyl) vanadate in Example 4.

0.5 grams of tri ($\alpha,\alpha,\alpha$-trifluoro-m-tolyl)-silanol (m.p. 72°–73° C.) was dissolved in 30 ml. of absolute benzene. To the solution was added, 0.115 grams of tris-(trimethyl-siloxy)-vanadium oxide. The mixture was refluxed for one hour by heating to boiling. From the reaction mixture, there was distilled off at atmospheric pressure, 20 ml. of benzene and the trimethyl silanol which formed. Finally after the addition of 20 ml. of toluene, another 20 ml. of a benzene toluene mixture was distilled off at atmospheric pressure. The remaining toluene solution evaporated under reduced pressure at 50° C. One obtained tris [tri ($\alpha,\alpha,\alpha$-trifluoro-m-tolyl)-siloxy] vanadium oxide [Molpeak = 1504].

By this procedure:
Tris-(trimethylsiloxy)-vanadiumoxide and
Tris-($\alpha,\alpha,\alpha$-trifluor-p-tolyl)-silanol were reacted to form
Tris-[tri-($\alpha,\alpha,\alpha$-trifluor-p-tolyl)-siloxy]-vanadiumoxide [Molpeak = 1504];
Tri-(p-fluorphenyl)-silanol, and tri-(trimethylsiloxy) vanadium oxide; and Triphenylsilanol were reacted in a mole ratio of 1:1:2 to form
(Tri-p-fluorphenyl)-siloxy-bis-(triphenylsiloxy)-vanadiumoxide; m.p. 203° C.;
Tris-(trimethylsiloxy)-vanadiumoxide,
Tri-(p-fluorphenyl)-silanol, and
Triphenylsilanol were reacted in a mole ratio of 1:2:1: to form
Bis-[tri-(p-fluorophenyl)-siloxy]-triphenylsiloxyvanadiumoxide, [Molpeak = 1000];
Tris-(trimethysiloxy)-vanadiumoxide, Tri-(p-bromophenyl)-silanol and
Cyclohexanol were reacted in a mole ratio of 1:2:1:to form
Bis-[tri-(p-bromphenyl)-siloxy]cyclohexyloxyvavadiumoxide. [Molpeak = 1184];
Tris-(trimethyl-siloxy)-vanadiumoxide; and Bis-(3-nitro-4-bromphenyl)-(4-bromphenyl)-silanol were reacted to form
Tris-[bis-(3-nitro-4-bromphenyl)-(4-bromphenyl)-siloxy]-vanadiumoxide[Molpeak = 600].

EXAMPLE 53

The starting material bis (3-nitro-4-bromophenyl)-silanol for use in Example 52 was prepared as follows:

1 g. of tri-(p-bromophenyl)-silanol was dissolved in sulfolane. To this solution there was added, dropwise at 10° C., 98 grams of sodium tetrafluoroborate [NaO$_2$BF$_4$] in 25 ml. of sulfolane. This addition was carried out in an apparatus which does not allow any water to enter into the reaction mixture. The reaction mixture was stirred for one hour at room temperature, after which saturated aqueous sodium bicarbonate solution was added thereto. After this addition, the reaction mixture was extracted with diethyl ether. The ether extract was washed with an aqueous saturated sodium sulfate solution and dried over sodium sulfate and evaporated at room temperature and reduced pressure. The residue was bis-(3-nitro-4-bromophenyl)-4-silanol which melted after crystalization from a nitrobenzenepetroleum ether mixture at 211° C.

EXAMPLE 54

This example is directed to the preparation of different catalyst that can be utilized in place to the tris(triphenylsilyl) vanadate in Example 4.

1 g. of tri(p-fluorophenyl) silanol was dissolved in 30 ml. of absolute benzene. To this solution, there was added 0.255 ml. of pyridine and 0.173 g. of vanadium oxytrichloride. Care was taken during this addition, to keep out any moisture from the reaction mixture. The resulting mixture was first stirred at room temperature and then heated for two hours at reflux conditions. After this period, the reaction mixture was cooled to 10° C. whereupon the pyridinium hydrochloride, which precipitated, was filtered off. The filtrate was dried under reduced pressure. The residue which resulted was tris [tri-(p-fluorophenyl)-siloxy]-vanadium oxide which had a melting point of 147° C. upon crystallization from n-heptane.

By the above procedure:

vanadium oxytrichloride was reacted with tri (p-chlorophenyl)-silanol (m.p. = 127°–128° C.) to produce tris [tri-(p-chlorophenyl)-siloxy]vanadium oxide (m.p. = 181° C.);

vanadium oxytrichloride was reacted with tri (p-bromophenyl) silanol, (m.p. = 120–121° C.) to produce tris[(p-bromophenyl)-siloxy]-vanadium oxide (m.p. = 175° C.); and vanadium oxytrichloride was reacted with tri-4-biphenylyl-silanol (m.p. = 199–200° C.) to produce tris [tri-(4-biphenylyl)-siloxy]vanadium oxide.

We claim:

1. A process for producing a compound of the formula:

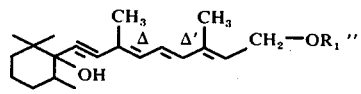

wherein
R$_1''$ is alkanoyl containing from 2 to 18 carbon atoms or aroyl and $\Delta$ represents a cis configuration; and
$\Delta'$ represents a trans configuration;
comprising treating a compound of the formula:

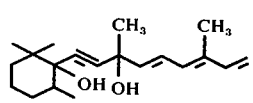

with an organic acid selected from the group consisting of an alkanoic acid or an aroic acid.

2. The process of claim 1 wherein said acid is an alkanoic acid.

3. The process of claim 1 wherein said acid is acetic acid.

4. The process of claim 1 wherein said acid is palmitic acid.

5. A compound of the formula

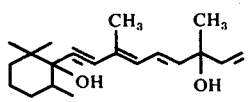

6. A process for producing a compound of the formula:

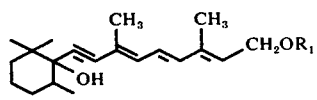

wherein $R_1$ is alkanoyl containing from 2 to 18 carbon atoms or aroyl;

comprising treating a compound of the formula:

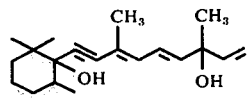

with an organic acid selected from the group consisting of an alkanoic acid or an aroic acid.

7. The process of claim 6 wherein said acid is an alkanoic acid.

8. The process of claim 7 wherein said acid is acetic acid.

9. The process of claim 7 wherein said acid is palmitic acid.

* * * * *